United States Patent
Boucher et al.

(10) Patent No.: US 10,533,024 B2
(45) Date of Patent: Jan. 14, 2020

(54) METHODS FOR SYNTHESIZING METAL MESOPORPHYRINS

(71) Applicant: INFACARE PHARMACEUTICAL CORPORATION, Trevose, PA (US)

(72) Inventors: Christopher P. Boucher, Newmarket (CA); David Roe, Rockwood (CA)

(73) Assignee: MALLINCKRODT HOSPTIAL PRODUCTS IP LIMITED, Dublin (IE)

( * ) Notice: Subject to any disclaimer, the term of this patent is extended or adjusted under 35 U.S.C. 154(b) by 0 days.

(21) Appl. No.: 16/125,190

(22) Filed: Sep. 7, 2018

(65) Prior Publication Data

US 2019/0002481 A1    Jan. 3, 2019

Related U.S. Application Data

(60) Continuation of application No. 15/603,654, filed on May 24, 2017, now abandoned, which is a division of application No. 14/875,141, filed on Oct. 5, 2015, now Pat. No. 9,688,705, which is a division of application No. 14/253,710, filed on Apr. 15, 2014, now Pat. No. 9,181,285, which is a division of application No. 13/435,868, filed on Mar. 30, 2012, now Pat. No. 8,735,574.

(60) Provisional application No. 61/532,301, filed on Sep. 8, 2011, provisional application No. 61/469,792, filed on Mar. 30, 2011, provisional application No. 61/469,791, filed on Mar. 30, 2011.

(51) Int. Cl.
    *C07D 487/22*    (2006.01)
    *C07F 7/22*      (2006.01)

(52) U.S. Cl.
    CPC .......... *C07F 7/2284* (2013.01); *C07D 487/22* (2013.01)

(58) Field of Classification Search
    CPC ................................................... C07D 487/22
    See application file for complete search history.

(56) References Cited

U.S. PATENT DOCUMENTS

| | | |
|---|---|---|
| 4,619,923 A | 10/1986 | Kappas et al. |
| 4,657,902 A | 4/1987 | Kappas et al. |
| 4,668,670 A | 5/1987 | Rideout et al. |
| 4,684,637 A | 8/1987 | Kappas et al. |
| 4,692,439 A | 9/1987 | Rideout et al. |
| 4,692,440 A | 9/1987 | Kappas et al. |
| 4,708,964 A | 11/1987 | Allen |
| 4,782,049 A | 11/1988 | Kappas et al. |
| 4,831,024 A | 5/1989 | Vreman et al. |
| 4,861,876 A | 8/1989 | Kessel |
| 4,900,871 A | 2/1990 | Ellis, Jr. et al. |
| 5,010,073 A | 4/1991 | Kappas et al. |
| 5,062,775 A | 11/1991 | Orth |
| 5,081,115 A | 1/1992 | Vreman et al. |
| 5,162,313 A | 11/1992 | Kappas et al. |
| 5,192,757 A | 3/1993 | Johnson et al. |
| 5,223,494 A | 6/1993 | Kappas et al. |
| 5,275,801 A | 1/1994 | Niedballa et al. |
| 5,371,199 A | 12/1994 | Therien et al. |
| 5,493,017 A | 2/1996 | Therien et al. |
| 5,665,869 A | 9/1997 | Ryland et al. |
| 5,756,723 A | 5/1998 | Therien et al. |
| 5,817,830 A | 10/1998 | Therien et al. |
| 5,883,246 A | 3/1999 | Brueckner et al. |
| 5,886,173 A | 3/1999 | Hemmi et al. |
| 5,889,181 A | 3/1999 | Kudrevich et al. |
| 5,912,341 A | 6/1999 | Hoffman et al. |
| 5,929,064 A | 7/1999 | Goel et al. |

(Continued)

FOREIGN PATENT DOCUMENTS

| | | |
|---|---|---|
| AU | 2012202684 B2 | 7/2014 |
| CA | 2448570 A1 | 12/2002 |

(Continued)

OTHER PUBLICATIONS

American Academy of Pediatrics, Provisional Committee for Quality Improvement and Subcommittee on Hyperbilirubinemia "Practice Parameter: Management of Hyperbilirubinemia in the Healthy Term Newborn" Oct. 1, 1994, Pediatrics 94(4):558-565.

Baker et al. "The Preparation of Mesoporphyrin IX and Etioporphyrin III" Aug. 1964, Analytical Biochemistry 8(4):512-518.

Bauer et al. "Pharmazeutische Technologie" 1993 published by George Thieme Verlag Stuttgart (New York) 4thh Ed. pp. 225-227.

Bauer et al. "Stability-Indicating High Performance Liquid Chromatographic Analysis of Tin Protoporphyrin and Other Free Acid Metalloporphyrins" 1988, Journal of Chromatography 445:429-432.

(Continued)

*Primary Examiner* — Brian E McDowell
(74) *Attorney, Agent, or Firm* — Shook, Hardy & Bacon LLP

(57) ABSTRACT

Embodiments describe methods of synthesizing metal mesoporphyrin compounds. In embodiments, a metal mesoporphyrin compound may be formed by hemin transmetallation and subsequent hydrogenation of the tin protoporphyrin IX to form a metal mesoporphyrin. In other embodiments, a method of synthesizing a metal mesoporphyrin compound comprises forming a protoporphyrin methyl ester from hemin and converting the protoporphyrin methyl ester intermediate to a metal mesoporphyrin compound through metal insertion and hydrogenation. In other embodiments, a metal mesoporphyrin compound may be formed from hemin by a hydrogen-free hydrogenation method to form a mesoporphyrin IX intermediate followed by metal insertion and hydrogenation. In embodiments, a method of synthesizing a metal mesoporphyrin compound comprises forming a mesoporphyrin IX dihydrochloride intermediate compound and converting the mesoporphyrin IX intermediate to a metal mesoporphyrin compound through metal insertion. In embodiments, a metal mesoporphyrin compound may be formed directly from hemin without isolation of any intermediates.

5 Claims, 5 Drawing Sheets

(56) References Cited

U.S. PATENT DOCUMENTS

| | | | |
|---|---|---|---|
| 5,955,603 | A | 9/1999 | Therien et al. |
| 5,973,141 | A | 10/1999 | Robinson et al. |
| 5,990,363 | A | 11/1999 | Wijesekera et al. |
| 6,004,530 | A | 12/1999 | Sagner et al. |
| 6,066,333 | A | 5/2000 | Willis et al. |
| 6,114,321 | A | 9/2000 | Platzek et al. |
| 6,124,452 | A | 9/2000 | DiMagno |
| 6,177,561 | B1 | 1/2001 | Sinn et al. |
| 6,194,566 | B1 | 2/2001 | Platzek et al. |
| 6,235,895 | B1 | 5/2001 | McEwan et al. |
| 6,420,553 | B1 | 7/2002 | Inoue et al. |
| 6,462,192 | B2 | 10/2002 | Robinson et al. |
| 6,818,763 | B2 | 11/2004 | Vukovich et al. |
| 7,375,216 | B2 | 5/2008 | Vukovich et al. |
| 7,777,028 | B2 | 8/2010 | Vukovich et al. |
| 7,960,371 | B2 | 6/2011 | Drummond et al. |
| 8,178,664 | B2 | 5/2012 | Vukovich et al. |
| 8,530,458 | B2 | 9/2013 | Drummond et al. |
| 8,735,574 | B2 | 5/2014 | Boucher et al. |
| 9,107,927 | B2 | 8/2015 | Drummond et al. |
| 2003/0100752 | A1 | 5/2003 | Robinson |
| 2003/0225264 | A1 | 12/2003 | Vukovich et al. |
| 2004/0097481 | A1 | 5/2004 | Levinson et al. |
| 2004/0210048 | A1 | 10/2004 | Vukovich et al. |
| 2004/0224886 | A1 | 11/2004 | Chen et al. |
| 2006/0222668 | A1 | 10/2006 | Drummond et al. |
| 2006/0222669 | A1 | 10/2006 | Drummond et al. |
| 2007/0087933 | A1 | 4/2007 | Purta et al. |
| 2008/0113955 | A1 | 5/2008 | Levinson et al. |
| 2008/0125585 | A1 | 5/2008 | Drummond et al. |
| 2008/0154033 | A1 | 6/2008 | Vukovich et al. |
| 2008/0242857 | A1 | 10/2008 | Martin et al. |
| 2008/0261939 | A1 | 10/2008 | Drummond et al. |
| 2008/0280934 | A1 | 11/2008 | Lugtenburg et al. |
| 2010/0280237 | A1 | 11/2010 | Vukovich et al. |
| 2011/0082292 | A1 | 4/2011 | Drummond et al. |
| 2012/0253033 | A1 | 10/2012 | Boucher et al. |
| 2013/0158362 | A1 | 6/2013 | Tulloch et al. |
| 2014/0005380 | A1 | 1/2014 | Drummond et al. |
| 2014/0228560 | A1 | 8/2014 | Boucher et al. |
| 2015/0051184 | A1 | 2/2015 | Drummond et al. |
| 2016/0000802 | A1 | 1/2016 | Drummond et al. |

FOREIGN PATENT DOCUMENTS

| | | |
|---|---|---|
| CA | 2665075 A1 | 3/2014 |
| CA | 2665075 C | 8/2014 |
| EP | 0199888 B1 | 11/1986 |
| EP | 0527016 A1 | 2/1993 |
| JP | 58501130 A | 7/1983 |
| JP | H01501627 A | 8/1989 |
| JP | 4939398 B1 | 3/2012 |
| KR | 101253541 | 4/2013 |
| MX | 302238 | 8/2013 |
| NZ | 576030 | 10/2012 |
| UA | 99904 C2 | 10/2012 |
| WO | 198902269 A1 | 3/1989 |
| WO | 199104667 A1 | 4/1991 |
| WO | 199428906 A1 | 12/1994 |
| WO | 199705152 | 2/1997 |
| WO | 200168099 A1 | 9/2001 |
| WO | 2003101999 A2 | 12/2003 |
| WO | 2004045546 A2 | 6/2004 |
| WO | 2005103056 A2 | 11/2005 |
| WO | 2006107806 A2 | 10/2006 |
| WO | 2008045377 A2 | 4/2008 |
| WO | 2008045378 A2 | 4/2008 |
| WO | 2012135686 A1 | 10/2012 |
| WO | 2013082559 A1 | 8/2013 |

OTHER PUBLICATIONS

Bettelheim et al. "Chapter 18. Proteins" 1998, General Organic & Biochemistry, 5th Ed. p. 596.

Bhutan I et al. "Randomized Placebo-Controlled Clinical Trial of Stannsoporfin (Sn-MP) to Prevent Severe Hyperbillirubinemia in Term and Near-Term Infants" Apr. 2004, Pediatric Research Abstract No. 2542.

Breslow et al. "Biochemical Properties of the Heme Oxygenase Inhibitor, Sn-Protoporphyrin" Mar. 5, 1986, The Journal of Biological Chemistry 261 (7):3135-3141.

Cannon et al. "Targeted Delivery of a Heme Oxygenase Inhibitor with a Lyophilized Liposomal Tim Mesoprophyrin Formulation" 1993, Pharmaceutical Research 1 0(5): 715-721.

Corwin et al. "A Synthetic Ferroporphyrin Complex That Is Passive to Oxygen" Aug.-Dec. 1946, Journal of the American Chemical Society 68:2473-2478.

Cowan et al. "Synthesis and Properties of Metal-Substituted Myoglobins" May 31, 1989, Inorganic Chemistry 28 (11):2074-2078.

Delaney et al. "Photophysical Properties of Sn-Porphyrins: Potential Clinical Implications" Apr. 1988, Pediatrics 81 (4):498-504.

Denissen "Synthesis of [119mSn]-Mesoporphyrin IX Dichloride" Dec. 1990, Journal of Labelled Compounds and Radiopharmaceuticals, XXVIII ( 12): 1421-1426.

Drummond "Control of Heme Metabolism by Synthetic Metalloporphyrins" 1987, Annals of New York Academy of Sciences 514:87-95.

Drummond et al. "An Experimental Model of Postnatal Jaundice in the Suckling Rat, Suppression of Induced Hyperbillirubinemia by Sn-Protoprophyrin" Jul. 1984, J. Clin. Invest. 74:142-149.

Drummond et al. "Chemoprevention of Severe Neonatal Hyperbilirubinemia" Oct. 2004, Seminars in Perinatology 28(5):365-368.

Drummond et al. "Prevention of neonatal hyperbillirubinemia by tin Protoporphyrin IX, a potent competitive inhibitor of heme oxidation" Oct. 1981, PNAS USA 78(10):6466-6470.

Drummond et al. "Reduction of the C2 and C4 Vinyl groups of Sn-Protoporphyrin to Form Sn-Mesoporphyrin Markedly Enhances the Ability of the Metalloporphyrin to Inhibit In Vivo Heme Catabolism" May 15, 1987, Archives of Biochemistry and Biophysics 255(1):64-74.

Ellfolk et al. "Separation of Porphyrins by Multiple Liquid-Liquid Partition" 1969, Acta. Chern. Scand. 23(3 part 1):846-858.

Eurasian Search Report dated Sep. 23, 2014 for EU 201400124.

European (Partial) Supplemental Search Report and Written Opinion dated Jun. 9, 2008, for EP 06749109 filed on Mar. 31, 2006, 10 pages.

European Search Report and Written Opinion dated Feb. 22, 2011 for EP 10014149 filed Mar. 31, 2006.

European Search Report and Written Opinion dated Nov. 24, 2010 for EP 10011800 filed Jun. 3, 2003, 6 pages.

European Supplemental Search Report dated Jan. 13, 2012 for EP 11176115 filed on Oct. 4, 2007, 9 pages.

European Supplemental Search Report dated Mar. 30, 2011 for EP 04811883 filed Nov. 24, 2004, 2 pages.

European Supplementary Search Report dated May 18, 2006, for EP 03736811 filed Jun. 3, 2003, 2 pages.

European Supplementary Search Report dated Sep. 12, 2006 for EP 03786815 filed Nov. 18, 2003, 3 pages.

European Supplementary Search Report and Written Opinion dated Aug. 28, 2014 for EP 12765367.

European Search Report and Written Opinion dated Apr. 22, 2015 for EP 12854066.

Galbraith et al. "Pharmacokinetics of Tin-Mesoporphyrin in Man and the Effects of Tin-Chelated Porphyrins of Hyperexcretion of Heme Pathway Precursors in Patients with Acute Inducible Porphyria" Jun. 1989, Hepatology 9(6):882-888.

Goodman et al. Goodman & Gilman's The Pharmaceutical Basis of Therapeutics, 6th Edition, MacMillan Publishing Co., NY 1980 (TOC).—Not Cited in Parent.

Hamori et al. "Suppression of Carbon Monoxide Excretion by Zinc Mesoporphyrin in Adult Wistar Rats: Evidence for Potent In Vivo Inhibition of Billirubin Production" Oct. 1988, Research Communications in Chemical Pathology and Pharmacology 62(1):41-48.

Hansen "Kemicterus in Term and Near-Term Infants—The Specter Walks Again" Oct. 2000, Acta Pediatrica 89(10):1155-1157.

(56) References Cited

OTHER PUBLICATIONS

Hermann et al. "Heterogeneous Metal-Insertion: a Novel Reaction with Porphyrins" Apr. 15, 1978, Canadian J. Chern. 56(8):1 084-1087.
Holmes et al. "Synthesis of Protoporphyrin8 1X Derivatives Bearing Extended Propionate Side-Chains" May 29, 2009, Arkivoc 5:5-16.
International Search Report and Written Opinion dated Apr. 3, 2008 for PCT Patent Application No. PCT/US 07/021486 filed on Apr. 10, 2007, 15 pages.
International Search Report and Written Opinion dated Feb. 9, 2007 for PCT Patent Application No. PCT/US04/39240, filed Nov. 24, 2004, six pages.
International Search Report and Written Opinion dated Mar. 27, 2008 for PCT Patent Application No. PCT/US07/21485 filed Oct. 4, 2007, nine pages.
International Search Report and Written Opinion dated May 24, 2007 for PCT Patent Application No. PCT/US06/12185, filed Mar. 31, 2006, eight pages.
International Search Report dated Aug. 31, 2012 for PCT Patent Application No. PCT/US12/31557 filed Mar. 30, 2012.
International Search Report dated Jun. 21, 2004 for PCT Patent Application No. PCT/US03/17426 filed Jun. 3, 2003, two pages.
International Search Report dated May 26, 2004 for PCT Patent Application No. PCT/US03/36885 filed Nov. 18, 2003, two pages.
International Search Report and Written Opinion dated Feb. 8, 2013 for PCT/US2012/067484.
Kaplan et al. "Determination of Isosmolar Blood Anticoagulant Solutions by the Freezing-Point Method" 1957, Clinical Chemistry 4(2): 142-145.
Kappas et al. "A Method for Interdicting the Development of Severe Jaundice in Newborns by Inhibiting the Production of Billirubin" Jan. 2004, Pediatrics 113:119-123.
Kappas et al. "A Single Dose of Sn-Mesoporphyrin Prevents Development of Severe Hyperbillirubinemia in Glucose-6-Phosphate Dehydrogenase-Deficient Newborns" Jul. 2001, Pediatrics 108:25-30.
Kappas et al. "Direct Comparison of Sn-Mesoporphyrin, an Inhibitor of Bilirubin Production, and Phototherapy in Controlling Hyperbilirubinemia in Term and Near-Term Newborns" Apr. 1995, Pediatrics 95(4):468-474.
Kappas et al. "Sn-Mesoporphyrin Interdiction of Severe Hyperbillirubinemia in Jehovah's Witness Newborns as an Alternative to Exchange Transfusion" Dec. 2001, Pediatrics 1 08(6):1374-1377.
Kappas et al. "Sn-Protoporphyrin Use in the Management of Hyperbillirubinemia in Term Newborns with Direct Coombs-Positive ABO Incompatability" Apr. 1, 1988, Pediatrics 81 (4):485-497.
Keren et al., "Identifying Newborns at Risk of Significant Hyperbilirubinemia: A Comparison of Two Recommended Approaches," 2005, Arch Dis Child 90: 415-421.
Lomova et al. "Advances in the Synthesis of Complex Compounds or Porphyrins with Highly-Charged Cations of p-, d- and f-" 1993, Koordinatsionnaya Khimiya 19(3):171-184 (with Eng. Translation).
Final Office Action dated Apr. 9, 2019 in U.S. Appl. No. 13/691,677, 15 pages.
Martinez et al. "Control of Severe Hyperbillirubinemia in Full-Term Newborns with the Inhibitor of Billirubin Production Sn-Mesoporphyrin" Jan. 1999, Pediatrics 1 03(1):1-5.
Morris "Asymmetric Hydrogenation, Transfer Hydrogenation and Hydrosilyation of Ketones Catalyzed by Iron Complexes" May 28, 2009, Chemical Society Reviews 38:2282-2291.
Non-Final Office Action dated Jan. 30, 2007, for U.S. Appl. No. 10/812,156, filed Mar. 29, 2004, ten pages.
Non-Final Office Action dated Oct. 20, 2003, for U.S. Appl. No. 10/453,815, filed Jun. 3, 2003, three pages.
Non-Final Office Action dated Oct. 22, 2007 for U.S. Appl. No. 11/239,769, filed Sep. 30, 2005, 8 pages.
Non-Final Office Action dated Oct. 23, 2007 for U.S. Appl. No. 11/096,359, filed Apr. 1, 2005, 8 pages.
Notice of Allowability dated Apr. 15, 2010, for U.S. Appl. No. 11/957,317, filed Dec. 14, 2007, 1 page.
Notice of Allowability dated Dec. 19, 2003, for U.S. Appl. No. 10/453,815, filed Jun. 3, 2003, 1 page.
Notice of Allowability dated Sep. 13, 2007, for U.S. Appl. No. 10/812,156, filed Mar. 29, 2004, two pages.
Porter et al. "Hyperbillirubinemia in the Term Newborn" Feb. 15, 2002, American Family Physician 65(4):599-606.
Reboucas et al. "A Simple, Catalytic H2-hydrogenation Method for the Synthesis of Fine Chemicals; Hydrogenation of Protoporphyrin IX Dimethyl Ester" Jul. 17, 2006, Tetrahedron Letters 47:5119-5122.
Reddy et al. "Tin-mesoporphyrin in the Treatment of Severe Hyperbilirubinemia in a Very-low-birth-weight Infant" 2003, Journal of Perinatology 23:507-508.
Sacerdoti et ai. "Role of the Heme Oxygenases in Abnormalities of the Mesenteric Circulation in Cirrhotic Rats" Nov. 4, 2003, The Journal of Pharmacology and Experimental Therapeutics 308(2):636-643.
Shenouda et al. "The Pharmacokinetics (PK) of Stannsoporfin in Healthy Adult Volunteers are Dose-Proportionate" Oct. 2004, American College of Clinical Pharmacology 44:1185-1186.
Simionatto et al. "Studies on the Mechanism of Sn-Protoporphyrin Suppression of Hyperbillirubinemia. Inhibition of Heme Oxidation and Billirubin Production" Feb. 1985, J. Clin. Invest. 75:513-521.
Sisson et al. "Sn-Protoporphyrin Blocks the Increase in Serum Billirubin Levels that Develops Postnatally in Gunn Rats" Mar. 1988, J. Exp. Med. 167:1247-1252.
Stokowski "Investigational Drug to Prevent Severe Jaundice" Oct. 2004, Advances in Neonatal Care 4(5):257.
Subcommittee on Hyperbilirubinemia "American Academy of Pediatrics Clinical Practice Guideline: Management of Hyperbilirubinemia in the Newborn Infant 35 or More Weeks of Gestation" Jul. 2004, Pediatrics 114(1):297-316.
Sugihara et al. "Determination of Vanadyl Porphyrins by Demetalation with Hydrogen Bromide-Formic Acid" Nov. 1964, Analytical Chemistry 36(12):2374-2376. 1-7.
Suresh et al. "Metalloporhyrins for Treatment of Unconjuagated Hyperbillirubinemia in Neonates (Review)" 2003 (e-published Jan. 20, 2003), Cochrane Collaboration of Systematic Reviews 1: 1-15.
Swarbrick "Encyclopedia of Pharmaceutical Technology" 2007, Informa Healthcare USA, Inc. 3rd Ed. 6:3768-3775.
Taylor "Metalloporphyrins. II. Cobalt and Manganese Mesoporphyrins in Coordination with Nitrogenous Bases" Sep. 1, 1940, Journal of Biological Chemistry 135(2):569-595.
Ushio et al. "Asymmetric Reduction of Ortho-Multisubstituted Benzophenones Catalyzed by Diamine-ZN-diol Complexes" Apr. 18, 2005, Tetrahedron Letters 46:2903-2906.
Valaes et al. "Control of Hyperbillirubinemia in Glucose-6-Phosphate Dehydrogenase-deficient Newborns using an Inhibitor of Billirubin Production, Sn-Mesoporphyrin" May 1998, Pediatrics 101(5):1-7.
Valaes et al. "Control of Jaundice in Preterm Newborns by an Inhibitor of Bilirubin Production: Studies With Tin-Mesoporphyrin" Jan. 1994, Pediatrics 93(1): 130-140.
Varvarigou et al., "Transcutaneous Bilirubin Nomogram for Prediction of Significant Neonatal Hyperbilirubinemia," Sep. 2009, Pediatrics, 124(4), 1052-1059.
Zvezdina et al. "Metal Exchange Reactions Between Cadmium Protoporphyrin and Cobalt and Zinc Chlorides in Acetonitrile and Dimethyl Sulfoxide" Jan. 1, 2006, Russian J. oflnorgan. Chern. 51(1):120-125.
Summons to Attend Oral Proceedings dated Jan. 25, 2018 in European Patent Application No. 15185138.3, 5 pages.

METHODS FOR SYNTHESIZING METAL MESOPORPHYRINS

CROSS-REFERENCE TO RELATED APPLICATIONS

This application is a continuation of U.S. application Ser. No. 15/603,654 filed on May 24, 2017, which is a divisional application of U.S. application Ser. No. 14/875,141 filed on Oct. 5, 2015, now U.S. Pat. No. 9,688,705, which issued on Jun. 27, 2017, which is a divisional application of U.S. application Ser. No. 14/253,710 filed on Apr. 15, 2014, now U.S. Pat. No. 9,181,285 which issued on Nov. 10, 2015, which is a divisional application of U.S. application Ser. No. 13/435,868 filed on Mar. 30, 2012, now U.S. Pat. No. 8,735,574 which issued on May 27, 2014, and claims priority to U.S. Provisional Patent Applications No. 61/469,791 filed on Mar. 30, 2011, No. 61/469,792 filed on Mar. 30, 2011, and No. 61/532,301 filed on Sep. 8, 2011 and each entitled "Methods for Synthesizing Metal Mesoporphyrins," the entire contents of each of which are hereby incorporated by reference.

GOVERNMENT INTERESTS

Not applicable

PARTIES TO A JOINT RESEARCH AGREEMENT

Not applicable

INCORPORATION BY REFERENCE OF MATERIAL SUBMITTED ON A COMPACT DISC

Not applicable

BACKGROUND

Not applicable

BRIEF SUMMARY OF THE INVENTION

Embodiments described herein are generally directed to methods of synthesizing metal mesoporphyrin compounds.

In some aspects, a method of synthesizing a metal mesoporphyrin compound comprises transmetallating hemin and hydrogenating the metal protoporphyrin IX. In some embodiments, the hemin is transmetallated in the presence of ferrous sulfate. In some embodiments, the metal protoporphyrin IX is hydrogenated using dilute ammonium hydroxide, dimethyl formamide or n-methyl pyrrolidinone. In some embodiments, the metal mesoporphyrin is precipitated using methyl tert-butyl ether (MTBE). In embodiments, the metal may comprise tin, iron, zinc, chromium, manganese, copper, nickel, magnesium, cobalt, platinum, gold, silver, arsenic, antimony, cadmium, gallium, germanium, palladium, or the like. In some embodiments, tin is the inserted metal. In embodiments, tin is inserted into mesoporphyrin to make stannsoporfin using tin oxide, tin chloride, tin sulfate, tin bromide, tin oxalate, tin pyrophosphate hydrate, tin 2-ethylhexanoate, tin methanesulfonic acid, or tin trifluromethanesulfonate.

In some aspects, a method of synthesizing a metal mesoporphyrin compound comprises forming a protoporphyrin methyl ester from hemin and converting the protoporphyrin methyl ester intermediate to a metal mesoporphyrin compound through metal insertion and hydrogenation. In some embodiments, metal insertion yields a metal protoporphyrin dimethyl ester intermediate. In further embodiments, the metal protoporphyrin dimethyl ester is hydrogenated in dichloromethane over palladium catalyst to form a metal mesoporphyrin dimethyl ester. In embodiments, the metal mesoporphyrin dimethyl ester is heated in dilute ammonium hydroxide to form the metal mesoporphyrin compound. In embodiments, the metal may comprise tin, iron, zinc, chromium, manganese, copper, nickel, magnesium, cobalt, platinum, gold, silver, arsenic, antimony, cadmium, gallium, germanium, palladium, or the like. In some embodiments, tin is the inserted metal. In embodiments, tin is inserted into mesoporphyrin to make stannsoporfin using tin oxide, tin chloride, tin sulfate, tin bromide, tin oxalate, tin pyrophosphate hydrate, tin 2-ethylhexanoate, tin methanesulfonic acid, or tin trifluromethanesulfonate.

In some aspects, a method of synthesizing a metal mesoporphyrin compound comprises forming a mesoporphyrin IX intermediate from hemin by a hydrogen-free hydrogenation, inserting a metal into the intermediate, and hydrogenating the metallated intermediate to form the metal mesoporphyrin compound. In embodiments, the metal may comprise tin, iron, zinc, chromium, manganese, copper, nickel, magnesium, cobalt, platinum, gold, silver, arsenic, antimony, cadmium, gallium, germanium, palladium, or the like. In some embodiments, tin is the inserted metal. In embodiments, tin is inserted into mesoporphyrin to make stannsoporfin using tin oxide, tin chloride, tin sulfate, tin bromide, tin oxalate, tin pyrophosphate hydrate, tin 2-ethylhexanoate, tin methanesulfonic acid, or tin trifluromethanesulfonate.

In embodiments, a method of synthesizing a metal mesoporphyrin compound comprises forming a mesoporphyrin IX dihydrochloride intermediate compound and converting the mesoporphyrin IX intermediate to a metal mesoporphyrin compound through metal insertion. In embodiments, the metal may comprise tin, iron, zinc, chromium, manganese, copper, nickel, magnesium, cobalt, platinum, gold, silver, arsenic, antimony, cadmium, gallium, germanium, palladium, or the like. In some embodiments, tin is the inserted metal. In embodiments, tin is inserted into mesoporphyrin using tin oxide, tin chloride, tin sulfate, tin bromide, tin oxalate, tin pyrophosphate hydrate, tin 2-ethylhexanoate, tin methanesulfonic acid, or tin trifluromethanesulfonate. In some embodiments, the metal mesoporphyrin halide is stannsoporfin.

In embodiments, a metal mesoporphyrin halide may be formed directly from hemin without isolation of any intermediates. In embodiments, a method of synthesizing a metal mesoporphyrin may comprise hydrogenation of hemin and subsequent insertion of metal. In some embodiments, no intermediate compound is isolated. In embodiments, the metal may comprise tin, iron, zinc, chromium, manganese, copper, nickel, magnesium, cobalt, platinum, gold, silver, arsenic, antimony, cadmium, gallium, germanium, palladium, or the like. In some embodiments, tin is the inserted metal. In embodiments, tin is inserted into mesoporphyrin using tin oxide, tin chloride, tin sulfate, tin bromide, tin oxalate, tin pyrophosphate hydrate, tin 2-ethylhexanoate, tin methanesulfonic acid, or tin trifluromethanesulfonate. In some embodiments, the metal mesoporphyrin halide is stannsoporfin.

DESCRIPTION OF DRAWINGS

For a fuller understanding of the nature and advantages of the present invention, reference should be had to the following detailed description taken in connection with the accompanying drawings, in which.

DETAILED DESCRIPTION

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

It must also be noted that, as used herein and in the appended claims, the singular forms "a", "an", and "the" include plural reference unless the context clearly dictates otherwise. Thus, for example, reference to a "compound" is a reference to one or more compounds and equivalents thereof known to those skilled in the art, and so forth.

As used herein, the term "about" means plus or minus 10% of the numerical value of the number with which it is being used. Therefore, about 50% means in the range of 45%-55%.

By "pharmaceutically acceptable", it is meant the carrier, diluent or excipient must be compatible with the other ingredients of the formulation and not deleterious to the recipient thereof.

In some aspects, embodiments are directed to a pharmaceutical composition comprising a compound described herein and a pharmaceutically acceptable carrier or diluent, or an effective amount of a pharmaceutical composition comprising a compound described herein and a pharmaceutically acceptable carrier or diluent.

Embodiments herein generally relate to novel processes for the preparation of metal mesoporphyrin halides. In embodiments, a metal mesoporphyrin compound may be formed by hemin transmetallation and subsequent hydrogenation of the metal protoporphyrin to form a metal mesoporphyrin halide. In other embodiments, a method of synthesizing a metal mesoporphyrin halide comprises forming a protoporphyrin methyl ester from hemin and converting the protoporphyrin methyl ester intermediate to a metal mesoporphyrin halide through metal insertion and hydrogenation. In other embodiments, a metal mesoporphyrin halide may be formed from hemin by a hydrogen-free hydrogenation method to form a mesoporphyrin IX intermediate followed by metal insertion into the mesoporphyrin IX intermediate and hydrogenation of the metallated intermediate to form the metal mesoporphyrin halide.

Figure 3:
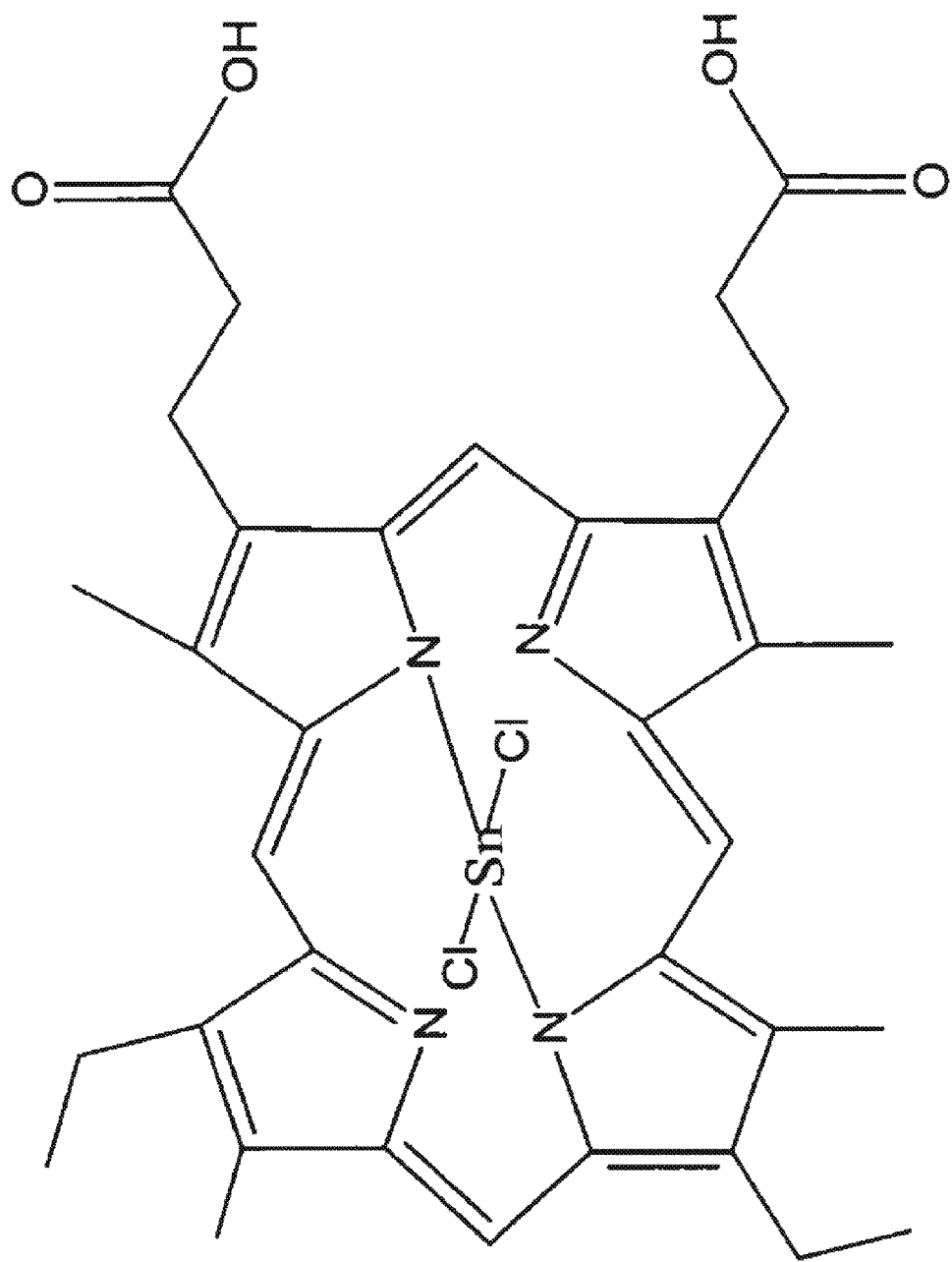
FIG. 3 illustrates the structure of stannsoporfin (B992).

Tin (IV) mesoporphyrin IX dichloride or stannsoporfin is a chemical compound having the structure indicated in FIG. 3. It has been proposed for use, for example, as medicament in the treatment of various diseases including, for example, psoriasis and infant jaundice. Stannsoporfin may also inhibit heme metabolism in mammals, to control the rate of tryptophan metabolism in mammals, and to increase the rate at which heme is excreted by mammals.

The insertion of metal into mesoporphyrin IX dihydrochloride to obtain metal mesoporphyrin halide is described above with specific reference to tin, to prepare stannsoporfin, a known pharmaceutical and a specific preferred embodiment of the invention. It is not intended that the scope of the invention should be limited thereto, but is generally applicable to the preparation of mesoporphyrin halides, for example, but not limited to, mesoporphyrin chlorides of other metals such as, for example, iron, zinc, chromium, manganese, copper, nickel, magnesium, cobalt, platinum, gold, silver, arsenic, antimony, cadmium, gallium, germanium and palladium, among others.

In embodiments, a metal mesoporphyrin compound may be formed by hemin transmetallation and subsequent hydrogenation of the metal protoporphyrin IX to form a metal mesoporphyrin halide. In embodiments, hemin is transmetallated with a metal carrier, for example tin to form tin protoporphyrin, followed by hydrogenation in a solvent, such as n-methyl pyrrolidinone, dilute ammonium hydroxide, or dimethyl formamide. In some embodiments, the hemin may be subjected to transmetallation with or without the addition of ferrous sulfate. In some embodiments, the transmetallated hemin is treated with charcoal. In some embodiments, the product is isolated after hydrogenation by the addition of acetic acid or hydrochloric acid. In some embodiments, the final product is precipitated using MTBE. In some embodiments, the product is further purified by chromatography.

In other embodiments, a method of synthesizing a metal mesoporphyrin halide comprises forming a protoporphyrin methyl ester from hemin and converting the protoporphyrin methyl ester intermediate to a metal mesoporphyrin halide through metal insertion and hydrogenation. To form the methyl ester, hemin, pyridine, and dichloromethane may be agitated to form a solution. Ferrous sulfate, methanol, dichloromethane, and HCl gas may then be added to form an exothermic reaction. In embodiments, the exothermic reaction may then be held at reflux for a period of about 2 to about 5 hours. In embodiments, the reaction may further be washed with water and dilute ammonium hydroxide to form the protoporphyrin methyl ester. In embodiments, a metal may be inserted into the protoporphyrin methyl ester. In some embodiments, tin may be inserted into the protoporphyrin methyl ester using tin oxide, tin chloride, tin sulfate, tin bromide, tin oxalate, tin pyrophosphate hydrate, tin 2-ethylhexanoate, tin methanesulfonic acid, or tin trifluromethanesulfonate. In embodiments, the metal protoporphyrin dimethyl ester may be hydrogenated using an appropriate metal catalyst in a hydrogen atmosphere to form a metal mesoporphyrin dimethyl ester. In some embodiments, tin protoporphyrin dimethyl ester may be hydrogenated to form tin mesoporphyrin dimethyl ester. In embodiments, a metal mesoporphyrin halide may be formed by heating the metal mesoporphyrin dimethyl ester in dilute ammonium hydroxide. In some embodiments, stannsoporfin may be formed from tin mesoporphyrin dimethyl ester by heating the material at about 70° C. to about 80° C. in dilute ammonium hydroxide. For example, stannsoporfin may be formed by heating tin mesoporphyrin dimethyl ester to about 75° C. in dilute ammonium hydroxide. In some embodiments, the product may be further purified by chromatography.

Some embodiments describe a method of synthesizing a metal mesoporphyrin halide comprising forming a mesoporphyrin IX dihydrochloride intermediate compound and converting the mesoporphyrin IX dihydrochloride intermediate to a metal mesoporphyrin halide through metal insertion. In some embodiments, hemin is hydrogenated in formic acid, over an appropriate metal catalyst under a hydrogen atmosphere, at about 80° C. to about 101° C. for about 1 hour to about 3 hours. In further embodiments, hydrogenation of the hemin may continue for an additional time of about 24 hours to about 36 hours at about 40° C. to about 60° C. For example, hemin may be hydrogenated at about 85° C. to about 90° C. at about 60 psi of hydrogen for about 1 hour to about 2 hours followed and then at about 45° C. to about 50° C. for about 24 hours to about 36 hours. In some embodiments, the metal catalyst may be palladium, nickel, platinum, palladium on carbon, or the like. Upon completion of hydrogenation, the reaction may be cooled to about 20° C. to about 30° C., or about 20° C. to about 25° C., and optionally charged with powdered activated carbon, such as that sold under the trade name Darco KB-G. Optionally, the reaction may be agitated prior to filtration. The reaction may be filtered through a metal scavenger such as Hyflo Supercel to remove catalyst. Optionally, the filtrate solution may then be concentrated, for example by vacuum distillation. A solution of about 1N HCL may then be added over about 1 hour or more to precipitate the intermediate product. After filtration, the product is dried under a stream of nitrogen to yield a mesoporphyrin IX dihydrochloride.

Figure 1:
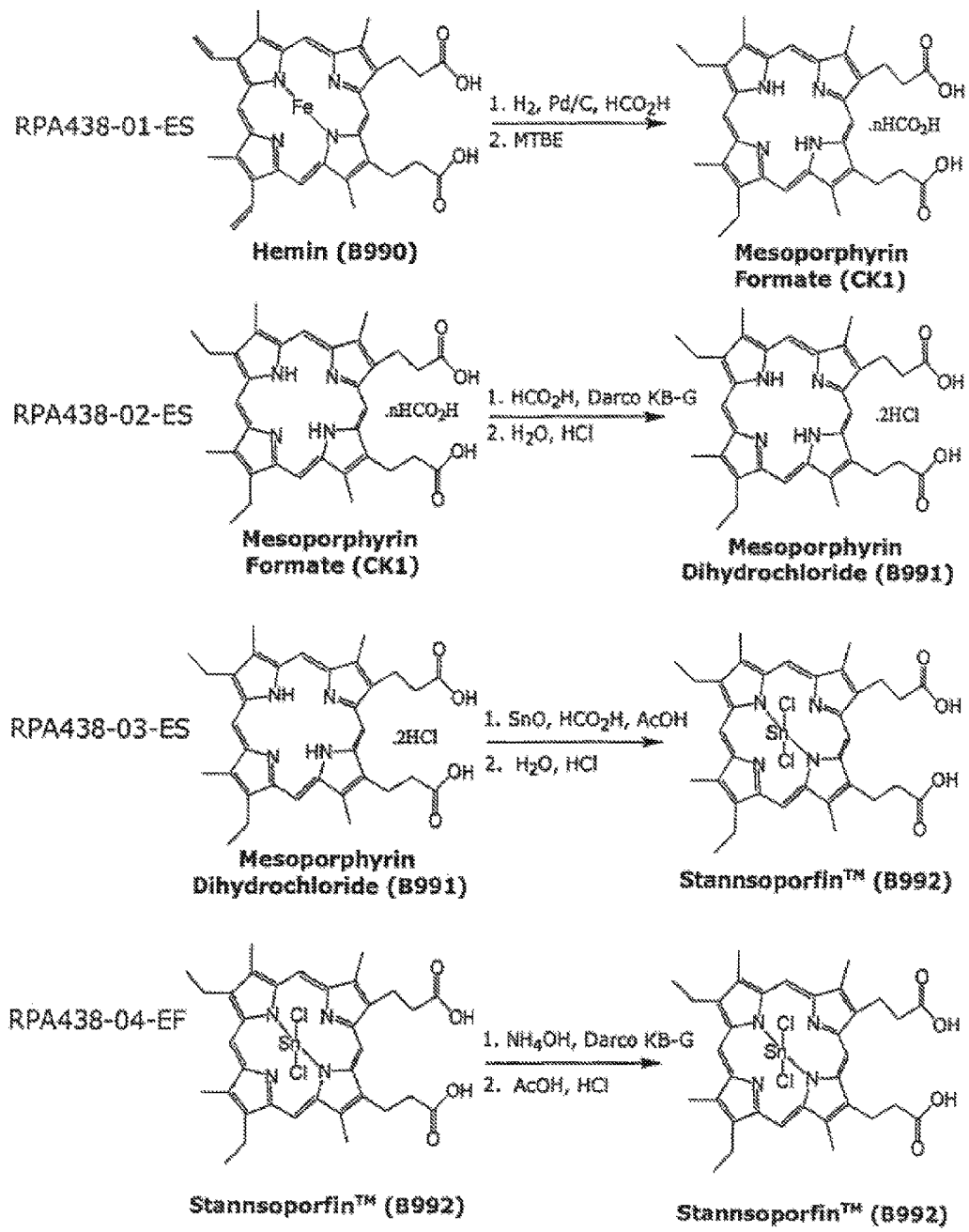
FIG. 1 illustrates an exemplary low temperature, oxygen-free synthesis of stannsoporfin and each constituent synthesis.

The second stage of the process according to one or more embodiments of the invention is illustrated in FIG. 1 as RPA438-03-ES with reference to tin as the inserted metal (standard tin oxide route). In embodiments, the metal may comprise tin, iron, zinc, chromium, manganese, copper, nickel, magnesium, cobalt, platinum, gold, silver, arsenic, antimony, cadmium, gallium, germanium, palladium, or the like. In some embodiments, the metal carrier is a tin (II) carrier. Tin (II) carriers such as tin (II) halides or tin (II) acetate may be used. In some embodiments, the tin carrier may be tin oxide, tin chloride, tin sulfate, tin bromide, tin oxalate, tin pyrophosphate hydrate, tin 2-ethylhexanoate, tin methanesulfonic acid, or tin trifluromethanesulfonate. In the standard tin oxide route, tin (II) oxide powder may be suspended in acetic acid. In embodiments, to this suspension may be added a solution of mesoporphyrin IX dihydrochloride in formic acid under a nitrogen atmosphere and warmed to about 60° C. to about 65° C. Once the reaction is complete, water may be added slowly and the reaction mixture may be slowly cooled to about 20° C. to about 30° C., or about 20° C. to about 25° C., agitated, and filtered. The filter cake may be rinsed with water, suspended in 1N HCl, and warmed to about 85° C. to about 95° C. for about 1 hours to about 3 hours. The suspension may be cooled to about 20° C. to about 30° C., or about 20° C. to about 25° C., agitated, and filtered and dried under nitrogen to yield crude tin mesoporphyrin IX dichloride.

In an exemplary embodiment, tin (II) oxide (SnO, 1.7 kg) powder may be suspended in about 40.5 L of acetic acid at about 20° C. to about 25° C. and then warmed to about 60° C. to about 65° C. under nitrogen. To this suspension may be added a solution of mesoporphyrin IX dihydrochloride (B991, 2.1 kg) in about 10.5 L formic acid over a period of about 6 hours. The reaction may be carried out under a nitrogen atmosphere at about 60° C. to about 65° C. for a minimum of about 12 hours. The reaction may be monitored by HPLC. Once the reaction is complete, about 17 L of water may be added over about 0.5 hours. The reaction mixture is then cooled to about 20° C. to about 25° C. over about 0.5 hours, agitated for about 1 to about 3 hours and then filtered. The filter cake may be rinsed with distilled water (USP), suspended in about 1N HCl and warmed to about 85° C. to about 95° C. for about 1 to about 3 hours. The suspension may then be cooled to about 20° C. to about 25° C., agitated for about 0.5 hours, filtered, rinsed with distilled water (USP) and dried under nitrogen to yield about 1.3 to about 1.5 Kg of crude tin mesoporphyrin IX dichloride (stannsoporfin).

In embodiments, mesoporphyrin IX dihydrochloride may be subjected to heating with a metal carrier in acetic acid, in the presence of an oxidant, at reflux (oxidative reflux process). In embodiments, the metal may comprise tin, iron, zinc, chromium, manganese, copper, nickel, magnesium, cobalt, platinum, gold, silver, arsenic, antimony, cadmium, gallium, germanium, palladium, or the like. In some embodiments, the metal carrier is a tin (II) carrier. Tin (II) carriers such as tin (II) halides or tin (II) acetate may be used. In some embodiments, the tin carrier may be tin oxide, tin chloride, tin sulfate, tin bromide, tin oxalate, tin pyrophosphate hydrate, tin 2-ethylhexanoate, tin methanesulfonic acid, or tin trifluromethanesulfonate.

In an exemplary embodiment, the heating is performed with aeration, for example, by an inflow of about 6% oxygen mixed with nitrogen for about 24 hours to about 48 hours. Air inflow may also be used to aerate during heating. The reaction may also be carried out in the presence of suitable acetate counter ions include ammonium, sodium or potassium ions. Oxidants such as oxygen from air or in pure form as well as hydrogen peroxide may also be used. In an exemplary embodiment, mesoporphyrin IX formate is subjected to heating with tin (II) oxide in acetic acid, buffered with ammonium acetate, and the reaction is conducted with aeration, at reflux. The ammonium acetate can be eliminated. The metallated mesoporphyrin may be isolated from the reaction mixture by the addition of water, followed by filtration. In embodiments, prior to drying, the cake may triturated into hot, dilute hydrochloric acid, preferably at concentration of about 0.1N-6N and at an elevated temperature of about 90° C. to about 100° C. In embodiments, the reaction yields a crude metal mesoporphyrin IX dichloride. In some embodiments, the reaction yields a crude tin (IV) mesoporphyrin IX dichloride.

The metal mesoporphyrin dichloride so obtained may be further purified by dissolving the product in an aqueous inorganic base solution, preferably dilute ammonium hydroxide, followed by treatment with charcoal. In embodiments, the product may then be re-precipitated by addition to an acid solution, such as acetic acid, hydrochloric acid or a mixture thereof. The above dissolving charcoal treatment and re-precipitation steps may be repeated a number of times, typically about 1 to 3 times in order to ensure the desired purity. Prior to drying, the cake is triturated in hot, dilute hydrochloric acid of a concentration of about 0.1N to about 6N, at an elevated temperature of about 90° C. to about 100° C., in order to remove any residual ammonium salts. In embodiments, the metallated mesoporphyrin chloride product (tin (IV) mesoporphyrin IX dichloride or stannsoporfin) is obtained. In some embodiments, the tin mesoporphyrin chloride product (tin (IV) mesoporphyrin IX dichloride or stannsoporfin) is obtained. In further embodiments, the final product, ex. stannsoporfin, is isolated by chromatography.

In an exemplary embodiment using tin mesoporphyrin dichloride, crude tin mesoporphyrin IX dichloride (1.7 Kg) may be dissolved in 2% ammonium hydroxide (22 L). A pH check may be performed to ensure the pH is ≥9.0. The solution may be treated with Darco KB-G (0.1 Kg) and Hyflo Supercel (0.2 Kg), agitated for a period of 1 to 2 hours and filtered to remove solids. The filtrate may then be added drop wise to acetic acid (44 L) containing hydrochloric acid (31%, 2.7 L), keeping the temperature at 20° C. to about 25° C. A pH check may again be performed to ensure pH≤1.0. The resultant suspension may be agitated for 1 to 2 hours under nitrogen prior to isolating the product by filtration. The wet cake may then be triturated in 3N HCl (35 L) at 85° C. to about 90° C. and agitated for about 16 hours to about 18 hours to convert the crystalline form to monomer and remove residual ammonium salts. The suspension may be cooled to 20° C. to about 25° C. and the product isolated by filtration. The product cake may be rinsed with 0.3N HCl (16 L) and dried under a stream of nitrogen to yield about 1.2 to about 1.6 Kg of Stannsoporfin.

In embodiments, the metal may comprise tin, iron, zinc, chromium, manganese, copper, nickel, magnesium, cobalt, platinum, gold, silver, arsenic, antimony, cadmium, gallium, germanium, palladium, or the like. Preparation of mesoporphyrin halides of these other metals simply entails a substitution of a halide such as chloride, bromide or iodide of the chosen metal in place of stannous chloride in the process described, in substantially equivalent amounts.

In other embodiments, a metal mesoporphyrin halide may be formed from hemin by a hydrogen-free hydrogenation method to form a mesoporphyrin IX intermediate followed by metal insertion into the mesoporphyrin IX intermediate and hydrogenation of the metallated intermediate to form the metal mesoporphyrin halide. Mesoporphyrin may be obtained by reacting hemin with ferrous sulfate, palladium on carbon, and poly(methylhydrosiloxane) (PMHS) in formic acid at reflux and further hydrogenated with PMHS. The product may be isolated as mesoporphyrin formate from formic acid and methyl tertbutyl ether. The product may then be carried through the dihydrochloride formation process outlined above. In other embodiments, the hemin was reacted with ferrous sulfate, palladium on carbon, and poly(methylhydrosiloxane) (PMHS) in formic acid and then concentrated by rotary evaporation to remove formic acid. The ensuing solids may be isolated by filtration and carried through the standard tin oxide route. The resulting filtrate may then be concentrated and dissolved in dilute ammonium hydroxide and precipitated by addition to acetic acid or hydrochloric acid. In some embodiments, the iron may be removed from hemin using ferrous sulfate prior to the PMHS hydrogenation. In some embodiments, the product is further purified by chromatography.

In any of the above embodiments, the reactants, intermediates, and/or products can undergo additional steps of purification. In some embodiments, the additional purification comprises treating the reactant, intermediate, or product with diatomaceous earth and/or activated carbon. In one embodiment, the treating of the reactant, intermediate, or product with diatomaceous earth and/or activated carbon comprises dissolving or suspending the reactant, intermediate, and/or product in a solvent, adding diatomaceous earth and/or activated carbon, filtering off the diatomaceous earth and/or activated carbon, and recovering the reactant, intermediate, or product from the filtrate. In some embodiments, the additional purification comprises triturating the reactant, intermediate, or product with hot acid, such as about 0.1 to 6N HCl in water, preferably about 3N HCl in water. In some embodiments, one, two, or three of the steps of treating with diatomaceous earth, treating with activated carbon, and triturating with hot acid are performed sequentially, in any order, and can be repeated as desired.

In certain embodiments, a metal mesoporphyrin halide may be formed directly from hemin without isolation of any intermediates. In some embodiments, metal mesoporphyrin compound is synthesized without isolating a mesoporphyrin formate intermediate or a mesoporphyrin dihydrochloride intermediate. In some embodiments, the metal mesoporphyrin may be synthesized using any of the above described methods without isolating the mesoporphyrin dihydrochloride intermediate. In some embodiments, the metal mesoporphyrin may be synthesized using any of the above described methods without isolating an intermediate. In some embodiments, the metal mesoporphyrin may be synthesized using the standard tin oxide route or the oxidative-reflux process described above without isolating the mesoporphyrin dihydrochloride intermediate. In some embodiments, the metal mesoporphyrin may be synthesized using the standard tin oxide route or the oxidative-reflux process described above without isolating an intermediate. In some embodiments, a method of synthesizing stannsoporfin comprises hydrogenating hemin and heating the reaction in the presence of a metal carrier. In some embodiments, the heating takes place in a nitrogen atmosphere. In some embodiments, a method of synthesizing stannsoporfin comprises hydrogenating hemin and heating the resulting reaction with a metal carrier in acetic acid, in the presence of an oxidant, at reflux. In embodiments, the metal may comprise tin, iron, zinc, chromium, manganese, copper, nickel, magnesium, cobalt, platinum, gold, silver, arsenic, antimony, cadmium, gallium, germanium, palladium, or the like. In some embodiments, the metal carrier is a tin (II) carrier. Tin (II) carriers such as tin (II) halides or tin (II) acetate may be used. In some embodiments, the tin carrier may be tin oxide, tin chloride, tin sulfate, tin bromide, tin oxalate, tin pyrophosphate hydrate, tin 2-ethylhexanoate, tin methanesulfonic acid, or tin trifluromethanesulfonate.

In some embodiments, hemin is hydrogenated in formic acid, over an appropriate metal catalyst under a hydrogen atmosphere, at about 80° C. to about 101° C. for about 1 hour to about 3 hours. In further embodiments, hydrogenation of the hemin may continue for an additional time of about 24 hours to about 36 hours at about 40° C. to about 60° C. For example, hemin may be hydrogenated at about 85° C. to about 90° C. at about 60 psi of hydrogen for about 1 hour to about 2 hours followed and then at about 45° C. to about 50° C. for about 24 hours to about 36 hours. In some embodiments, the metal catalyst may be palladium, nickel, platinum, palladium on carbon, or the like. Upon completion of hydrogenation, the reaction may be cooled to about 20° C. to about 30° C., or about 20° C. to about 25° C., and optionally charged with powdered activated carbon, such as that sold under the trade name Darco KB-G. Optionally, the reaction may be agitated prior to filtration. The reaction may be filtered through a metal scavenger such as Hyflo Supercel to remove catalyst. Optionally, the filtrate solution may then be concentrated, for example, by vacuum distillation.

In any of the above embodiments, the reactants, intermediates, and/or products can undergo additional steps of purification. In some embodiments, the additional purification comprises treating the reactant, intermediate, or product with diatomaceous earth and/or activated carbon. In one embodiment, the treating of the reactant, intermediate, or product with diatomaceous earth and/or activated carbon comprises dissolving or suspending the reactant, intermediate, and/or product in a solvent, adding diatomaceous earth and/or activated carbon, filtering off the diatomaceous earth and/or activated carbon, and recovering the reactant, intermediate, or product from the filtrate. In some embodiments, the additional purification comprises triturating the reactant, intermediate, or product with hot acid, such as about 0.1 to about 6N HCl in water, preferably about 3N HCl in water. In some embodiments, one, two, or three of the steps of treating with diatomaceous earth, treating with activated carbon, and triturating with hot acid are performed sequentially, in any order, and can be repeated as desired.

In another embodiment, a method of making a metal mesoporphyrin halide comprises the steps of: a) exposing a metallic hydrogenation catalyst to a hydrogen atmosphere to form pre-hydrogenated catalyst; and b) contacting hemin with the pre-hydrogenated catalyst and maintaining the hemin and catalyst under one or more cycles having a combination of temperature, hydrogen pressure, and time sufficient to remove iron from the hemin and reduce the vinyl groups of the hemin to ethyl groups, thus forming mesoporphyrin IX. In another embodiment, a method of making a metal mesoporphyrin halide comprises the steps of: a) exposing a metallic hydrogenation catalyst to a hydrogen atmosphere to form pre-hydrogenated catalyst; b) contacting hemin with the pre-hydrogenated catalyst and maintaining the hemin and catalyst under one or more cycles having a combination of temperature, hydrogen pressure, and time sufficient to remove iron from the hemin and reduce the vinyl groups of the hemin to ethyl groups, thus forming mesoporphyrin IX; and c) reacting mesoporphyrin IX with a metal salt to form a metal mesoporphyrin halide using a controlled rate of oxidation.

In embodiments, step b) of embodiments herein may be carried out at about 80° C. to about 100° C., preferably at about 85° C. to about 90° C., with hydrogen pressure at about 50 to about 70 psi, preferably at about 55 to about 60 psi, for about 1 to about 3 hours, preferably about 1 to about 1.5 hours; then at about 40° C. to about 60° C., preferably about 45° C. to about 50° C., with hydrogen pressure at about 50 to about 70 psi, preferably at about 55 to about 60 psi, for about 18 to about 48 hours, preferably about 24 hours.

In one embodiment, the metallic hydrogenation catalyst comprises palladium, palladium on carbon, platinum, platinum on carbon, nickel, or nickel-aluminum catalyst. In another embodiment, the metallic hydrogenation catalyst is palladium. In another embodiment, the metallic hydrogenation catalyst is palladium on carbon.

Embodiments herein also include insertion of tin into mesoporphyrin to make stannsoporfin using tin oxide, tin chloride, tin sulfate, tin bromide, tin oxalate, tin pyrophosphate hydrate, tin 2-ethylhexanoate, tin methanesulfonic acid, or tin trifluromethanesulfonate. In particular embodiments, tin is inserted into mesoporphyrin using tin oxide, tin chloride or tin 2-ethylhexanoate.

In embodiments, the mesoporphyrin IX hydrochloride may be treated with a tin (II) salt in an organic solvent, such as acetic acid, under oxidizing conditions, which yields the desired product, tin (IV) mesoporphyrin IX dichloride (stannsoporfin). For example, mesoporphyrin IX dihydrochloride and tin (II) chloride may be placed in a vessel, and acetic acid may be added at about 20° C. to about 30° C., preferably at about 20° C. to about 25° C. The suspended reagents are agitated for at least about 30 minutes. With vigorous agitation, the mixture is warmed under an inert atmosphere (such as nitrogen or argon) to reflux.

In an embodiment, the invention embraces a method of inserting tin into mesoporphyrin IX, comprising reacting the mesoporphyrin IX with a tin salt in the absence of a proton scavenger.

In another embodiment, the invention embraces a method of inserting tin into mesoporphyrin IX, comprising reacting the mesoporphyrin IX with a tin salt at a controlled rate of oxidation. In one embodiment, the mesoporphyrin IX is reacted with a tin salt in a reaction vessel having a headspace, and the rate of oxidation is controlled by introducing an oxygen-containing gas into the headspace of the reaction vessel. In another embodiment, the oxygen-containing gas introduced into the headspace of the reaction vessel is about 3% to about 22% oxygen in an inert gas, such as nitrogen. In another embodiment, the oxygen-containing gas introduced into the headspace of the reaction vessel is air. In another embodiment, the oxygen-containing gas introduced into the headspace of the reaction vessel is about 4% to about 15% oxygen in an inert gas, such as nitrogen. In another embodiment, the oxygen-containing gas introduced into the headspace of the reaction vessel is about 5% to about 10% oxygen in an inert gas, such as nitrogen. In another embodiment, the oxygen-containing gas introduced into the headspace of the reaction vessel is about 6% oxygen in an inert gas, such as nitrogen. In another embodiment, the oxygen-containing gas introduced into the headspace of the reaction vessel is about 6% oxygen in nitrogen.

Embodiments herein also include insertion of tin into mesoporphyrin to make stannsoporfin using tin oxide, tin chloride, tin sulfate, tin bromide, tin oxalate, tin pyrophosphate hydrate, tin 2-ethylhexanoate, tin methanesulfonic acid, or tin trifluromethanesulfonate.

Other porphyrin compounds and tetrapyrroles can also be metallated using the procedures described herein, including, but not limited to, porphyrins such as deuteroporphyrins and deuteroporphyrin IX 2,4-bis(ethylene glycol) (8,13-bis(1,2-dihydroxyethyl)-3,7,12,17-tetramethyl-21H,23H-porphine-2,18-dipropionic acid). Additional porphyrin compounds which can be metallated using the procedures described herein include, but are not limited to, coproporphyria, cytoporphyrins, etioporphyrins, hematoporphyrins, mesoporphyrins, phylloporphyrins, protoporphyrins, pyrroporphyrins, rhodoporphyrins, uroporphyrins, and phytoporphyrins. A comprehensive listing of porphyrin compounds is given at World-Wide-Web, chem. qmul.ac.uk/iupac/tetrapyrrole/; the porphyrins described therein are hereby incorporated by reference herein as porphyrins which can be metallated using the procedures described herein.

This invention and embodiments illustrating the method and materials used may be further understood by reference to the following non-limiting examples.

Example 1

Stannsoporfin may be prepared by a reverse route in which hemin is transmetallated with tin oxide to form tin protoporphyrin followed by hydrogenation in either n-methyl pyrrolidinone, dilute ammonium hydroxide, or dimethyl formamide.

Reactions were carried out wherein hemin was subjected to the RPA438-03-ES tin oxide chemistry (see FIG. 1), with and without the addition of ferrous sulfate. After heating the reaction mixture to 90° C. for 2 hours under nitrogen to effect dissolution of the hemin, the reaction was continued at 60° C. to about 65° C. overnight. HPLC analysis confirmed the reaction complete for the reaction which did not have ferrous sulfate, and 98.4% complete for the reaction which did. Both reactions were isolated by the standard water addition with identical yields of 97.3%.

Based on the success of these experiments, the reaction without ferrous sulphate was scaled up to 40 g to prepare material to study the subsequent transformations. See Table 1 for results.

TABLE 1

ANALYTICAL RESULTS, TIN PROTOPORPHYRIN

| Experiment | Description | Overall Yield (%) From Hemin | HPLC Purity (% ala) | HPLCAssay (% w/w) |
|---|---|---|---|---|
| 1165-CB-141-1 | Tin Protoporphyrin | 92.5 | 98.1 | 104.9 |

Dilute Ammonium Hydroxide:

A hydrogenation was carried out in dilute ammonium hydroxide over palladium catalyst. The solvent volume and concentration was chosen to match that used in the RPA438-04-EF purification process illustrated in FIG. 1.

Figure 4:
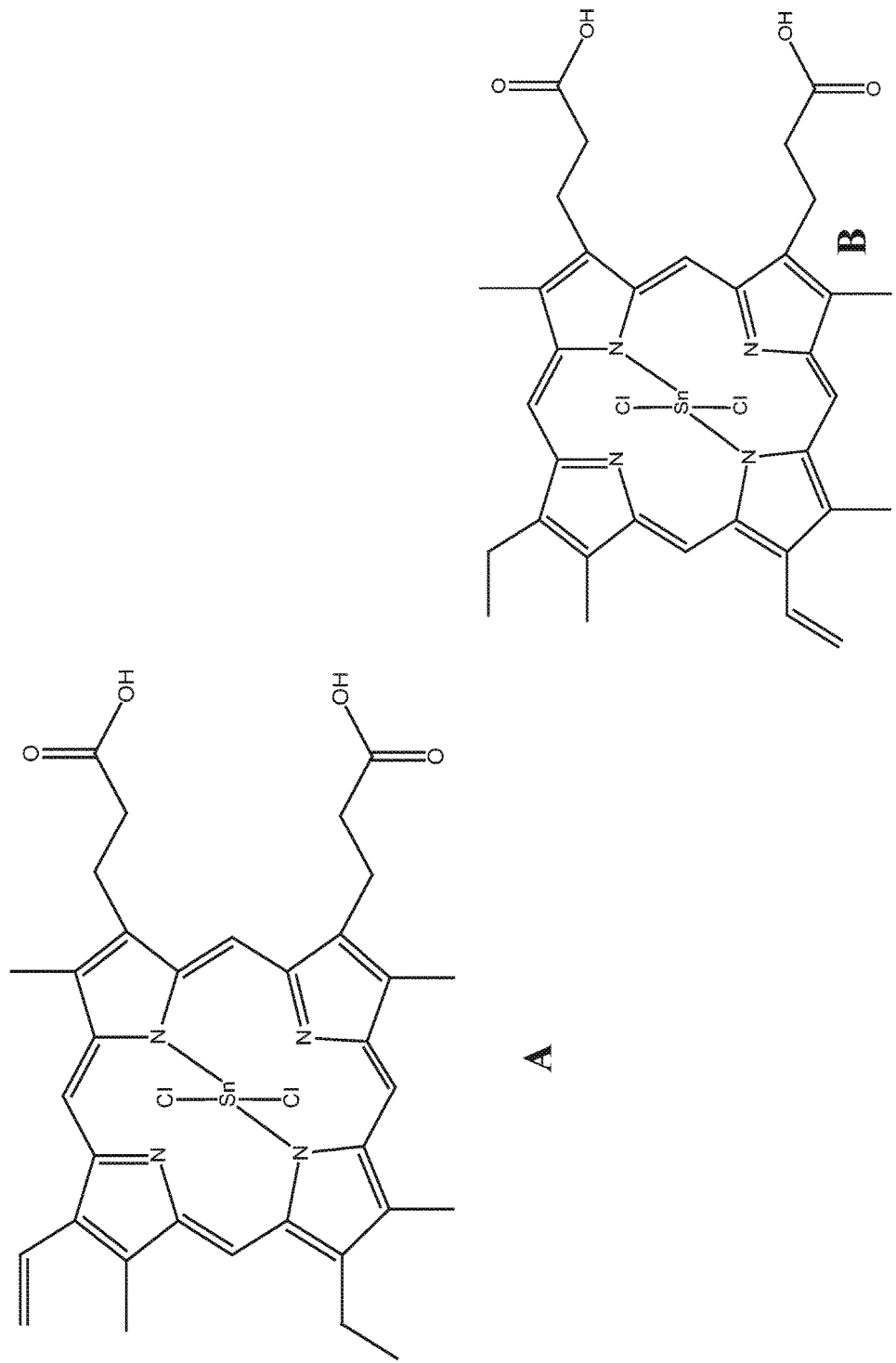
FIG. 4 illustrates the structure of monovinyl intermediates (A) CJ9 and (B) CKO.
Figure 5:
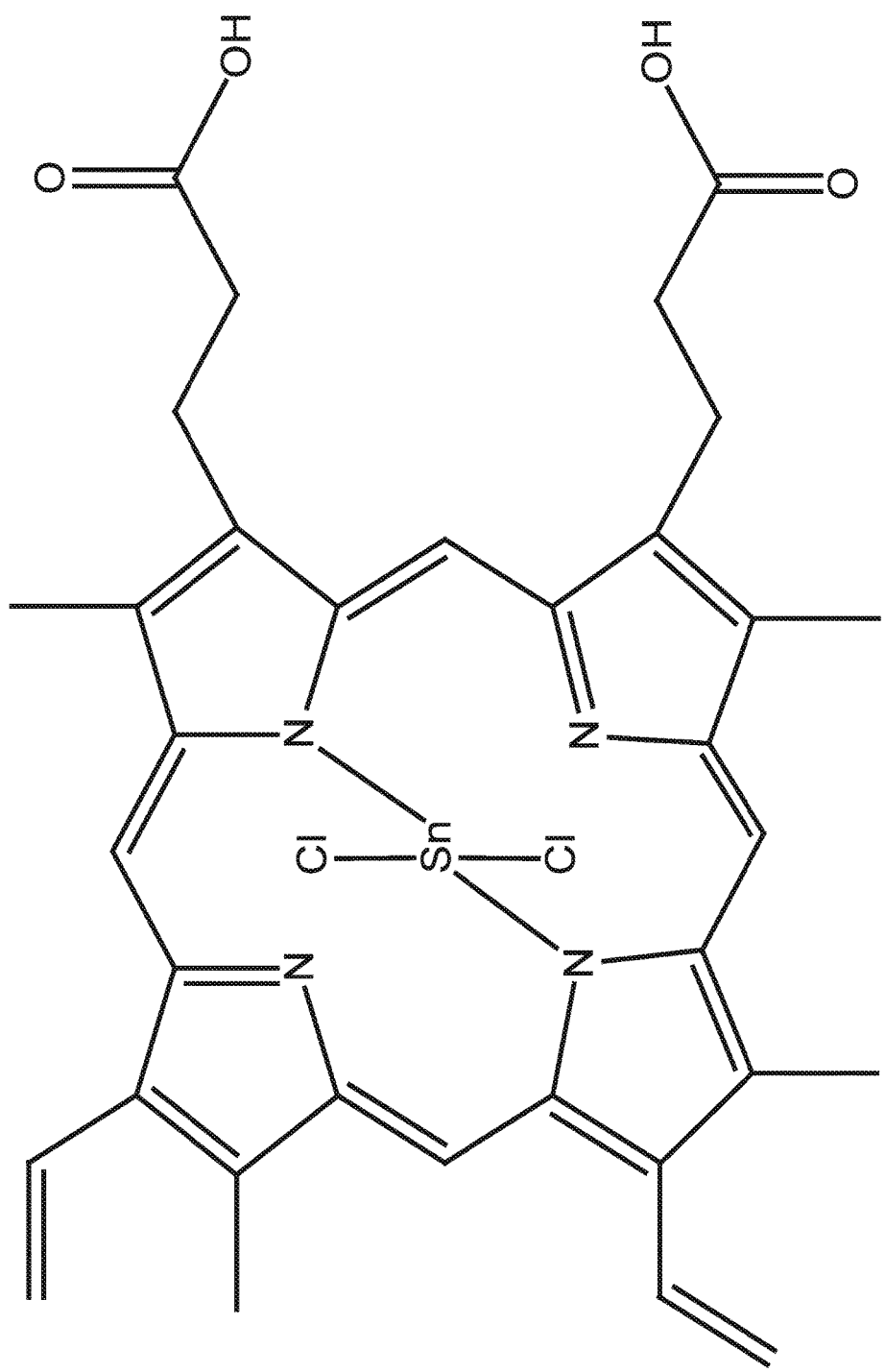
FIG. 5 illustrates the structure of tin protoporphyrin (CH8).

The initial IPC analysis for this reaction seemed to indicate that no reaction had occurred. However, when the product was isolated and analyzed by the final product purity method, it was determined that the solid contained 18.2% stannsoporfin (B992; FIG. 3), 14.7 & 39.5% of the monovinyl intermediates (CJ9/CKO; FIG. 4), and 27.6% of tin protoporphyrin (CH8; FIG. 5).

The ammonium hydroxide reaction was repeated with a charcoal pre-treatment. The first IPC analysis after reacting overnight showed 83.3% stannsoporfin (B992), 15.9% of the monovinyl intermediates (CJ9/CKO), and 0.7% tin protoporphyrin (CH8). The reaction mixture was filtered and the hydrogenation continued with fresh catalyst to drive the reaction to completion in less than 2 hours. The product was isolated by addition to acetic acid/hydrochloric acid (as with the RPA438-04-EF purification process illustrated in FIG. 1) and triturated in hot 1N HCl for 1 hour. The yield from this transformation was 78%. The product from the reaction was carried through the purification process with a yield of 91.4%. The overall yield for the process was 65.9% with a purity of 98.8% (See Table 2, Ref.: 1165-CB-172-1).

Dimethyl Formamide:

An hydrogenation was carried out using dimethyl formamide (DMF) solvent and palladium on carbon. Both the starting material and product can be dissolved at 50 parts allowing for catalyst removal upon reaction completion. After reacting overnight in process analysis (IPC) analysis showed 35.5% B992, 28 & 11% monovinyl intermediates, and 25.4% of tin protoporphyrin. The DMF solution at the IPC stage was analyzed by liquid chromatography-mass spectrometry (LC/MS) to confirm the identity of each peak in the IPC HPLC.

N-Methyl Pyrrolidinone (NMP):

NMP was evaluated as a solvent for the hydrogenation. After reacting overnight at 50° C./60 psi, IPC analysis showed 51% stannsoporfin (B992), 20% & 10% monovinyl intermediates (CJ9/CKO), and 18.5% tin protoporphyrin (CH8). During this reaction it was observed that all hydrogen seemed to be taken up within the first 1 to 2 hours of reaction suggesting that the catalyst may have been poisoned. The reaction was then warmed to 90° C./60 psi overnight again. IPC analysis showed that the reaction had proceeded further to 68% stannsoporfin (B992), 21 and 9% monovinyl intermediates (CJ9/CKO), and 2.1% tin protoporphyrin (CH8), suggesting that the catalyst hadn't been completely poisoned.

Based on the assumption that the catalyst was being poisoned during the reaction, an NMP solution of tin protoporphyrin (CH8) was treated with Darco-KBG activated carbon for 1 hour and filtered prior to charging the catalyst for hydrogenation. After reacting overnight at 50° C./60 psi IPC analysis showed 94.2% stannsoporfin (B992) and 1.7% monovinyl intermediates (CJ9/CKO). This reaction mixture was split into 2 equal parts and added to either 300 parts of water or 300 parts of methyl tert-butyl ether (MTBE) and cooled to about 0° C. to about 5° C. for about 2 hours. Upon filtration, it was discovered that there was little to no precipitation with water, but MTBE afforded a nice filterable solid with a yield of 90%.

The NMP hydrogenation with charcoal treatment was scaled up to 10 g. The first IPC analysis after reacting at 50° C./60 psi overnight showed 92.5% stannsoporfin (B992), 3.6 and 2.4% monovinyl intermediates (CJ9/CKO), and 0.4% tin protoporphyrin (CH8). The reaction mixture was filtered prior to re-subjecting to hydrogenation with fresh catalyst to drive the reaction to completion after 2 further hours. The product was isolated by addition to a copious quantity of methyl tert-butyl ether in a yield of 119.9% (product contains residual NMP). The product from the reaction was carried through the purification process with a yield of 108.0% (likely due to residual solvents). The purity obtained was 98.2%. (See Table 2, Ref.: 1165-CB-171-1).

TABLE 2

ANALYTICAL RESULTS, REVERSE ROUTE

| Experiment | Description | Overall Yield (%) From Hemin | HPLC Purity (% a/a) | HPLC Assay (% w/w) |
|---|---|---|---|---|
| 1165-CB-171-1 | Stannsoporfin | 119.9 | 98.2 | 47.0 |
| | Reverse route prep NMP hydrogenation | | RRt % ala | |
| | | | 0.06 0.13 | |
| | | | 0.25 0.11 | |
| | | | 0.42 0.20 | |
| | | | 0.62 0.23 | |
| | | | 0.66 0.10 | |
| | | | 0.88 0.10 | |
| | | | 0.9 0.10 | |
| | | | Others <0.10 | |
| 1165-CB-172-1 | Stannsoporfin Reverse route prep NH4OH hydrogenation | 65.9 | 98.8 | 80.8 |
| | | | RRt % ala | |
| | | | 0.09 0.13 | |
| | | | 0.25 0.09 | |
| | | | 0.88 0.10 | |
| | | | 0.9 0.05 | |
| | | | Others <0.14 | |

Example 2

Formation of Protoporphyrin Methyl Ester.

A 5 L reactor was charged with 20 g of hemin, 50 ml pyridine, and 200 ml of dichloromethane and agitated 10 minutes to form a solution, 50 g of Ferrous sulfate, 1000 ml of methanol, and 1000 ml of dichloromethane were then added. HCl gas was added slowly. The exothermic reaction eventually reached a reflux temperature of 41° C. (note: no heating was applied) and held at reflux for a period of 3 hours. TLC analysis confirmed the reaction was complete. The reaction was quenched with 1000 ml of water, which was followed by additional washes with water and dilute ammonium hydroxide. Then protoporphyrin methyl ester was isolated from dichloromethane/methanol in a yield of 50.4%.

Tin Insertion Followed by Hydrogenation.

Tin protoporphyrin dimethyl ester was prepared according to the standard tin oxide route, directly substituting protoporphyrin dimethyl ester for mesoporphyrin. The product was obtained in a yield of 77.7%

The tin protoporphyrin dimethyl ester was hydrogenated in dichloromethane over 5% palladium catalyst at 50 psi. After reaction overnight, the product was isolated by concentration by rotary evaporation in 100% yield. NMR analysis of the product suggested there was circa 10% unreacted starting material. However, upon re-subjecting the material to the hydrogenation conditions, no further change was noted and the reaction was carried forward as is.

Stannsoporfin was formed from the tin mesoporphyrin dimethyl ester by heating the material to 75° C. in dilute ammonium hydroxide. After 18 hours of reaction no further change was noted in the HPLC IPC, even after the addition of further ammonium hydroxide. The product was isolated from solution by addition into acetic acid/hydrochloric acid, as typically perfected during the purification, in a yield of 72.6%. The crude Stannsoporfin was purified according to the standard method and isolated in a yield of 72.2%. The overall process yield was 23.8% with a purity of 87.4% (See Table 3, Ref.: 1198-CB-003-1).

TABLE 3

ANALYSIS RESULTS, METHL ESTER ROUTE

| Experiment | Description | Overall Yield (%) From Hemin | HPLC Purity (% a/a) | | HPLC Assay (% w/w as is) |
|---|---|---|---|---|---|
| 1198-CB-003-1 | Stannsoporfin Methyl ester preparation | 23.8 | 87.4 | | 82.8 |
| | | | RRt | % a/a | |
| | | | 0.27 | 0.18 | |
| | | | 0.42 | 0.24 | |
| | | | 0.96 | 2.06 | |
| | | | 1.78 | 9.90 | |
| | | | Others | <0.05 | |

Example 3

Mesoporphyrin was obtained by reacting hemin with ferrous sulfate, palladium on carbon, and poly(methylhydrosiloxane) (PMHS) in formic acid at reflux. The reaction was split. Half was subjected to further hydrogenation with PMHS. The subsequent IPC showed the reaction to be complete. The product was isolated as CK1 (structure shown in FIG. 1) from formic acid and methyl tertbutyl ether (1198-CB-004-1). The isolation was very difficult due to solids (both products and wastes) sticking to the walls of the flask. This is likely due to the side product formed from PMHS which is expected to be a silicon grease. The initial reaction yielded 57.5% mesoporphyrin.

On the second half of the reaction, an attempt was made to isolate directly as B991 hydrochloride salt. However after following the standard process, no crystals were found. The solution was concentrated on by rotary evaporation to remove formic acid and the ensuing solids were isolated by filtration in a yield of 42.8%. A second crop of material was obtained from the filtrate the following day for an additional 11.2% yield. The two crops of material were combined and carried through the tin oxide process. After a standard reaction time no further B991 could be detected by HPLC. An attempt was made to isolate the product according to the standard process, however no solids were found. The filtrate was subsequently concentrated by rotary evaporation and the residue dissolved in dilute ammonium hydroxide and precipitated by addition to acetic acid/hydrochloric acid. The crude product was obtained in a yield of 26.6% (Table 4, Ref.: 1198-CB-011-1).

An attempt was also made to perform the iron removal from hemin using ferrous sulfate prior to the PMHS hydrogenation. This reaction was easier to handle since the iron salts and grease, both of which are insoluble, were not present in the reactor at the same time. The product was isolated in a yield of 62.1%. However, when the B991 (structure shown in FIG. 1) formation was attempted on this material it was found that no solids precipitated when hydrochloric acid was added to the formic acid solution.

The product from reaction 1198-CB-004-1 was carried through the B991 hydrochloride formation with a yield of 42.5%. The tin oxide process was repeated with this sample but the precipitation was allowed to stir overnight prior to filtration. The product from this reaction was obtained in a yield of 90.3%. The overall yield was 22.1% with 75.1% purity. (Table 4, Ref.: 1198-CB-013-1).

TABLE 4

ANALYSIS RESULTS, HYDROGEN-FREE PREPARATION

| Experiment | Description | Overall Yield (%) From Hemin | HPLC Purity (% a/a) | | HPLC Assay (% w/w as is) |
|---|---|---|---|---|---|
| 1198-CB-011-1 | Stannsoporfin Hydrogen-free preparation | 14.4 | 73.3 | | 25.2% |
| | | | RRt | % a/a | |
| | | | 0.38 | 0.63 | |
| | | | 0.42 | 0.32 | |
| | | | 0.70 | 0.44 | |
| | | | 0.76 | 0.41 | |
| | | | 0.79 | 0.54 | |
| | | | 0.89 | 21.95 | |
| | | | 1.71 | 0.31 | |
| | | | 2.14 | 0.26 | |
| | | | Others | <0.30 | |
| 1198-CB-013-1 | Stannsoporfin Hydrogen-free preparation | 22.1 | 75.1 | | 0.8% |
| | | | RRt | % a/a | |
| | | | 1.61 | 2.36 | |
| | | | 1.70 | 3.39 | |
| | | | 1.74 | 0.71 | |
| | | | 1.78 | 3.63 | |
| | | | 1.80 | 2.64 | |
| | | | 1.87 | 0.63 | |
| | | | 1.92 | 2.57 | |
| | | | 1.96 | 0.89 | |
| | | | 2.02 | 0.33 | |
| | | | 2.06 | 1.95 | |
| | | | 2.15 | 1.65 | |
| | | | 2.17 | 1.37 | |
| | | | 2.19 | 0.44 | |
| | | | 2.21 | 0.80 | |
| | | | 2.30 | 1.35 | |
| | | | Others | <0.20 | |

Example 4

Figure 2:
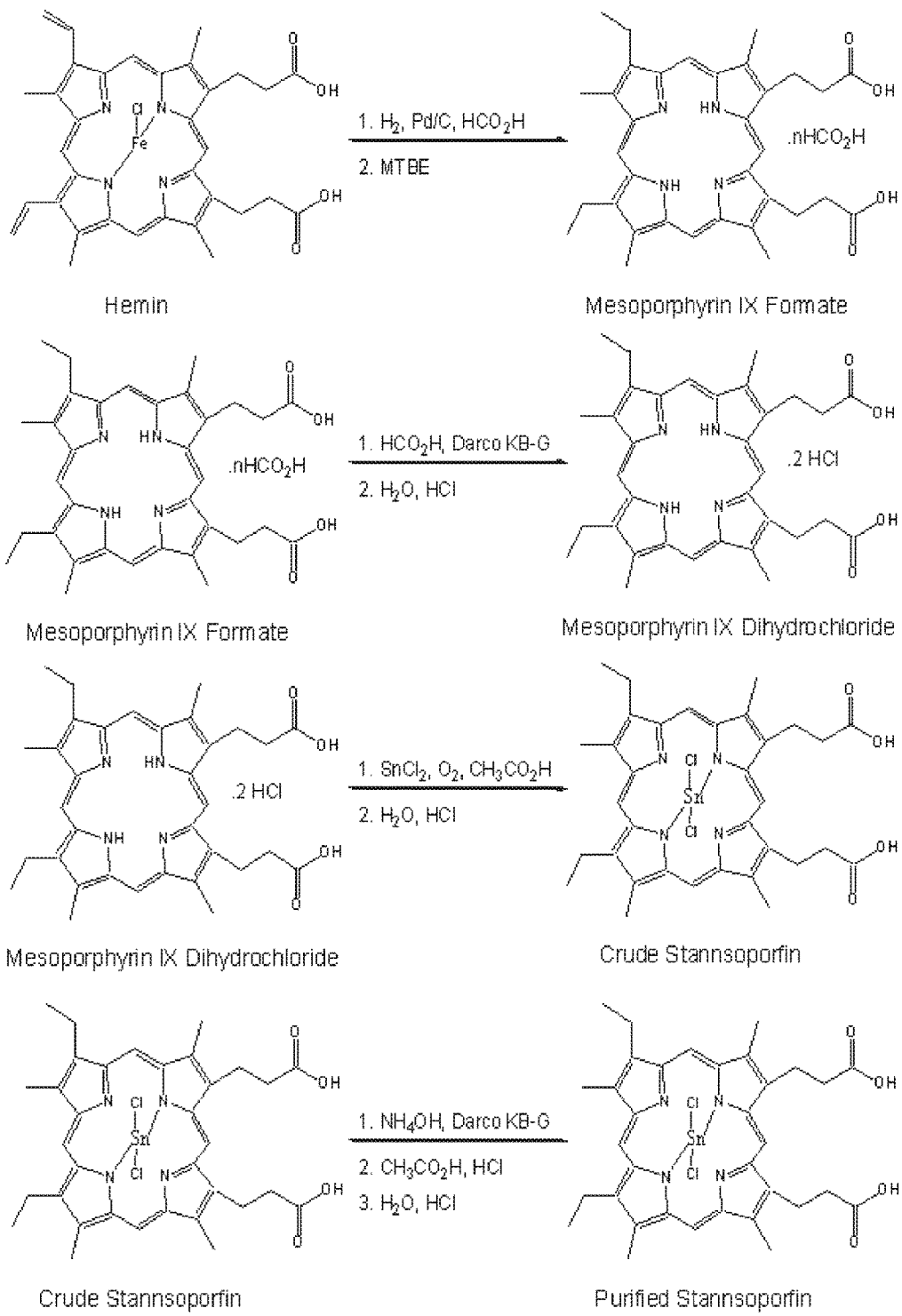
FIG. 2 illustrates an exemplary oxidative reflux synthesis of stannsoporfin.

Each tin carrier was evaluated according to an oxidative reflux for making stannsoporfin outlined in FIG. 2 and the low temperature, oxygen-free process outlined in FIG. 1. Initial screening reactions were carried out on a 150 mg scale. The results of the initial screening reactions in the oxidative process and in the low temperature, oxygen-free process are summarized in Tables 5 and 6, respectively.

TABLE 5

IPC RESULTS, ALTERNATIVE TIN SALTS IN OXIDATIVE PROCESS

| | | 24 hours | | 48 hours | |
|---|---|---|---|---|---|
| Experiment | Tin salt studied | B991 w.r.t. B992 (%) | B992 peak purity (% a/a) | B991 w.r.t. B992 (%) | B992 peak purity (% a/a) |
| 1198-CB-015 | Tin (II) Sulfate | 215.95 | 25.19 | 163.6 | 36.06 |
| 1198-CB-086-1 | Tin (II) oxide | 0.11 | 99.48 | 0.22 | 98.63 |
| 1198-CB-086-2 | Tin (II) bromide | 13.65 | 84.74 | 12.29 | 85.99 |
| 1198-CB-086-3 | Tin (II) oxalate | 49.5 | 62.76 | 48.6 | 61.05 |
| 1198-CB-086-4 | Tin (II) sulfide | No rxn | 0.00 | 10000.00 | 0.96 |
| 1198-CB-086-5 | Tin (II) pyrophosphate hydrate | 79.26 | 54.44 | 34.09 | 73.3 |
| 1198-CB-086-6 | Tin (II) 2-ethylhexanoate | 0.04 | 99.21 | 0.16 | 99.09 |
| 1198-CB-086-7 | Tin (II) methanesulfonic acid (50% aq solution) | 627 | 13.72 | 337.5 | 12.43 |
| 1198-CB-086-8 | Tin (II) trifluoromethanesulfonate | No rxn | 0.00 | 1007.95 | 6.16 |

TABLE 6

IPC RESULTS, ALTERNATIVE TIN SALTS IN LOW TEMPERATURE PROCESS

| | | 24 hours | | 48 hours | |
|---|---|---|---|---|---|
| Experiment | Tin salt studied | B991 w.r.t. B992 (%) | B992 peak purity (% a/a) | B991 w.r.t. B992 (%) | B992 peak purity (% a/a) |
| 1198-CB-014 | Tin (II) Sulfate | | | | |
| 1198-CB-088-1 | Tin (II) oxide | 1.50 | 94.53 | 0.64 | 99.36 |
| 1198-CB-088-2 | Tin (II) bromide | 34.04 | 73.09 | 9.45 | 91.36 |
| 1198-CB-088-3 | Tin (II) oxalate | 51.53 | 65.72 | 57.04 | 62.85 |
| 1198-CB-088-4 | Tin (II) sulfide | No rxn | 0.00 | No rxn | 0.00 |
| 1198-CB-088-5 | Tin (II) pyrophosphate hydrate | 296.65 | 24.48 | 241.01 | 28.43 |
| 1198-CB-088-6 | Tin (II) 2-ethylhexanoate | 0.29 | 99.71 | 1.17 | 98.84 |
| 1198-CB-088-7 | Tin (II) methanesulfonic acid (50% aq solution) | 4601.42 | 2.11 | 5540.91 | 1.76 |
| 1198-CB-088-8 | Tin (II) trifluoromethanesulfonate | 2442.82 | 3.90 | 2442.28 | 3.89 |

Based on the relative completeness of the reactions tin (II) bromide, tin (II) oxalate, and tin (II) ethylhexanoate were chosen for further study against a tin (II) oxide control. The tin insertion reactions were scaled to 5 g in order to prepare enough material for full analysis. The reactions were left for 96 hours instead of 48 due to an intervening weekend. Results are presented in Table 7.

TABLE 7

IPC RESULTS, ALTERNATE TIN SALTS IN LOW TEMPERATURE PROCESS

| | | 24 hours | | 96 hours | |
|---|---|---|---|---|---|
| Experiment | Tin salt studied | % B991 w.r.t. B992 | B992 peak purity (% a/a) | % B991 w.r.t. B992 | B992 peak purity (% a/a) |
| 1198-CB-091 | Tin (II) Oxide (CONTROL) | 8.2 | 91.55 | 3.5 | 96.6 |
| 1198-CB-092 | Tin (II) Bromide | 222.7 | 30.95 | 2841 | 3.40 |
| 1198-CB-093 | Tin (II) Oxalate | 3360 | 2.9 | 986.9 | 9.2 |
| 1198-CB-094 | Tin (II) Ethylhexanoate | 6.6 | 93.6 | 5.7 | 94.6 |

Due to their incompleteness, reactions 1198-CB-092 and 1198-CB-093 were discarded after 96 hours. Reactions 1198-CB-091 and 1198-CB-094 were isolated according to procedure. In both cases the observed yield upon drying was 79.7% (4.7 g). Both products were then carried through the final purification method (RPA438-04-ES) and the isolated products were analyzed. The tin (II) oxide (1198-CB-091) and tin (II) ethylhexanoate salts produced products with purities of 99.2% and 99.4%, respectively (Table 8).

TABLE 8

ANALYTICAL RESULTS, ALTERNATE TIN SALTS IN LOW TEMPERATURE PROCESS

| | Crude Products | | Purified Products | |
|---|---|---|---|---|
| Test Experiment | 1198-CB-096-1 Oxide | 1198-CB-097-1 Ethylhexanoate | 1198-CB-098-1 Oxide | 1198-CB-099-1 Ethylhexanoate |
| HPLC Purity (% a/a) | 98.8 | 99.3 | 99.2 | 99.4 |
| HPLC Assay (% w/w as is) | 95 | 100 | 101 | 100 |
| Description | N/A | N/A | Conforms | Conforms |
| IR identification | N/A | N/A | Conforms | Conforms |
| HPLC Identification | N/A | N/A | Conforms | Conforms |
| KF (% w/w) | N/A | N/A | <0.05 | <0.05 |
| Residual Solvents: Acetic & Formic (% w/w) | N/A | N/A | <0.1 | <0.1 |
| Solubility | N/A | N/A | Soluble | Soluble |

Example 5

Under RPA438-01-ES process, 5% palladium on carbon (50% wet, 0.6 Kg) is hydrogenated in formic acid (60 L) under an inert atmosphere at 40° C./(60 to 65 psi) for a period of 12 hours. Upon cooling, hemin (B990, 6 Kg) is added to the reaction vessel as a slurry in formic acid (60 L). The hemin is then hydrogenated at 85 to 90° C./60 psi for 1 to 2 hours followed by hydrogenation at 45 to 50° C./60 psi for a further 24 to 36 hours. The reaction is monitored by HPLC. Upon completion, the reaction is cooled to 20 to 25° C., charged with Darco KB-G, and filtered through Hyflo Supercel to remove catalyst. After filtration of the palladium catalyst, the reaction mixture was split into three equal portions by mass.

Referring to FIG. 1, one third of the reaction mixture was isolated as CK1 through the RPA438-01-ES process, which was then carried through the remainder of the process (1165-CB-155-1). The filtrate solution is concentrated by vacuum distillation to a residual volume, and 30 L of methyl tert-butyl ether (MTBE, 120 L) is added to the concentrate over a minimum of 1 hour to precipitate the intermediate product. The resultant suspension is cooled to −20 to −25° C. over 1 hour and agitated for 4 hours prior to filtration. The cake is dried under vacuum to remove residual MTBE, yielding 5 to 6 Kg mesoporphyrin IX formate (CK1, 85 to 100% yield).

One third was isolated directly as B991 through the RPA438-02-ES process and then carried through the remainder of the process (1165-CB-154-1). In the RPA438-02-ES, mesoporphyrin IX formate (CK1, 5 kg as free base) is dissolved in formic acid (22 L) and treated with active charcoal (Darco KB-G, 0.2 Kg) and Hyflo Supercel (0.4 Kg) and agitated for a period of 2 hours at 20 to 25° C. prior to filtration to remove solids. The filtrate is concentrated by vacuum distillation to a residual volume of 12 L. To this concentrate is added a solution of 1N HCl (13 L) over a minimum of 1 hour to precipitate the intermediate product. The resultant suspension is agitated at 20 to 25° C. under nitrogen for 2 hours prior to filtration. After filtration, the product is dried under a stream of nitrogen to yield 3.4 to 4.5 Kg of mesoporphyrin IX dihydrochloride (60 to 80% yield).

The remaining third of the reaction mixture was carried directly into the tin insertion reaction, RPA438-03-ES, as the filtered formic acid solution to make Stannsoporfin (B992) (1165-CB-153-1). In the RPA438-03-ES process, tin (II) oxide (SnO, 1.7 kg) powder is suspended in 40.5 L of acetic acid at 20 to 25° C. and then warmed to 60 to 65° C. under nitrogen. To this suspension is added a solution of mesoporphyrin IX dihydrochloride (B991, 2.1 kg) in 10.5 L formic acid over a period of 6 hours. The reaction is carried out under a nitrogen atmosphere at 60 to 65° C. for a minimum of 12 hours. The reaction is monitored by HPLC. Once the reaction is complete, 17 L of water is added over 0.5 hours. The reaction mixture is then cooled to 20 to 25° C. over 0.5 hours, agitated for 1 to 3 hours and then filtered. The filter cake is rinsed with distilled water (USP), suspended in 1N HCl and warmed to 85 to 95° C. for 1 to 3 hours. The suspension is then cooled to 20 to 25° C., agitated for 0.5 hours, filtered, rinsed with distilled water (USP) and dried under nitrogen to yield 1.3 to 1.5 Kg of crude tin mesoporphyrin IX dichloride (Stannsoporfin™, B992) (65 to 75% yield).

All B992 products obtained were also subjected to the final purification, RPA438-04-ES. Under the RPA438-04-ES process, crude tin mesoporphyrin IX dichloride (B992, 1.7 Kg) is dissolved in 2% ammonium hydroxide (22 L). A pH check is performed to ensure the pH is 2:9.0. The solution is treated with Darco KB-G (0.1 Kg) and Hyflo Supercel (0.2 Kg), agitated for a period of 1 to 2 hours and filtered to remove solids. The filtrate is then added drop wise to acetic acid (44 L) containing hydrochloric acid (31%, 2.7 L) keeping the temperature at 20 to 25° C. A pH check is again performed to ensure pH≤1.0. The resultant suspension is agitated for 1 to 2 hours under nitrogen prior to isolating the product by filtration. The wet cake is then triturated in 3NHCl (35 L) at 85 to 90° C. and agitated for 16 to 18 hours to convert the crystalline form to monomer. The suspension is cooled to 20 to 25° C. and the product is isolated by filtration. The product cake is rinsed with 0.3N HCl (16 L) and dried under a stream of nitrogen to yield 1.2 to 1.6 kg of Stannsoporfin API (70 to 90% yield). The results are summarized in Table 9.

TABLE 9

ANALYTICAL RESULTS, COMBINATION OF PROCESS STEPS

| | Test | | |
|---|---|---|---|
| | 1165-CB-153-1 | 1165-CB-154-1 | 1165-CB-155-1 |
| Experiment | No isolations | B991 isolation | B991/CK1 isolation (Control) |
| Yield (%) | 61.9 | 54.2 | 48.2 |
| HPLC Purity (% a/a) | 99.3 | 99.5 | 99.6 |
| | RRt   % a/a | RRt   % a/a | RRt   % a/a |
| | 0.22   0.06 | 0.07   0.06 | 0.88   0.05 |
| | 0.67   0.07 | 0.88   0.05 | 0.91   0.03 |

TABLE 9-continued

ANALYTICAL RESULTS, COMBINATION OF PROCESS STEPS

| | Test | | | | | |
|---|---|---|---|---|---|---|
| | 1165-CB-153-1 | | 1165-CB-154-1 | | 1165-CB-155-1 | |
| | 0.88 | 0.09 | 0.91 | 0.03 | 0.95 | 0.03 |
| | 0.91 | 0.06 | 0.95 | 0.03 | others | <0.05 |
| | 0.95 | 0.02 | others | <0.05 | | |
| | others | <0.05 | | | | |
| HPLC Assay (% w/w) | 96.8 | | 98.2 | | 99.5 | |
| Description | Conforms | | Conforms | | Conforms | |
| IR Identification | Conforms | | Conforms | | Conforms | |
| HPLC Identification | Conforms | | Conforms | | Conforms | |
| KF(% w/w) | 1.2 | | 0.4 | | 0.6 | |
| Residual Solvents (Acetone) | <500 | | <500 | | <500 | |
| Residual Solvents (Acetic & Formic) | 0.1 | | | | | |
| iron (ppm) | 6.55 | | 2.94 | | 2.84 | |
| Palladium (ppm) | 6.95 | | <2 | | <2 | |
| Solubility | Soluble | | Soluble | | Soluble | |
| Chloride (% w/w) | 7.3 | | 9.69 | | 9.97 | |

As can be seen in the table, each additional isolation decreased the overall yield for the process while increasing the assay and purity of the final product. All three materials passed specifications other than HPLC assay. The final purification method may increase the assay of the crude API. As such, each material was subjected to the final purification, RPA438-04-ES, for a second iteration and reanalyzed for HPLC purity and assay (Table 10).

TABLE 10

ANALYTICAL RESULTS, COMBINATION OF PROCESS STEPS WITH EXTRA PURIFICATION

| | Test | | | | | |
|---|---|---|---|---|---|---|
| | 1198-CB-020-1 | | 1198-CB-021-1 | | 1198-CB-022-1 (CONTROL) | |
| Starting Material | 1165-CB-153-1 | | 1165-CB-154-1 | | 1165-CB-155-1 | |
| Yield (%) | 92.0 | | 92.0 | | 94.0 | |
| HPLC Purity (% a/a) | RRt | % a/a | RRt | % a/a | RRt | % a/a |
| | 0.22 | 0.07 | 0.07 | 0.06 | 0.22 | 0.05 |
| | 0.39 | 0.05 | 0.14 | 0.05 | 0.88 | 0.05 |
| | 0.44 | 0.05 | 0.22 | 0.05 | 0.95 | 0.05 |
| | 0.64 | 0.05 | others | <0.05 | 1.08 | 0.13 |
| | others | <0.05 | | | others | <0.05 |
| HPLC Assay (% w/w) | 98 (as is) | | 98 (as is) | | 99 (as is) | |

With the exception of tin sulfide, all tin salts screened for use in the tin insertion reaction produced stannsoporfin by both the oxidative and non-oxidative processes. It is believed that higher purity may be achieved for all such tin salts. Using tin ethylhexanoate as the tin carrier, it was possible to prepare stannsoporfin of a quality equivalent to the product prepared using tin oxide.

Although the present invention has been described in considerable detail with reference to certain preferred embodiments thereof, other versions are possible. Therefore the spirit and scope of the appended claims should not be limited to the description and the preferred versions contained within this specification.

The invention claimed is:

1. A method of synthesizing a metal mesoporphyrin compound comprising:
    hydrogenating hemin with ferrous sulfate, palladium on carbon, and poly(methylhydrosiloxane) in formic acid to form a mesoporphyrin formate; converting the mesoporphyrin formate to a mesoporphyrin IX dihydrochloride intermediate compound;
    isolating the mesoporphyrin IX dihydrochloride intermediate compound; and inserting a metal into the mesoporphyrin IX dihydrochloride intermediate.

2. The method of claim 1, wherein the metal may be selected from tin, iron, zinc, chromium, manganese, copper, nickel, magnesium, cobalt, platinum, gold, silver, arsenic, antimony, cadmium, gallium, germanium, and palladium.

3. The method of claim 2, wherein the metal is tin.

4. The method of claim 3, wherein the tin is inserted using tin oxide, tin chloride, tin sulfate, tin bromide, tin oxalate, tin pyrophosphate hydrate, tin 2-ethylhexanoate, tin methanesulfonic acid, or tin trifluromethanesulfonate.

5. The method of claim 1, wherein the metal mesoporphyrin compound is stannsoporfin.

* * * * *